United States Patent [19]

Kitsnik

[11] 4,053,354
[45] Oct. 11, 1977

[54] METHOD AND DEVICE FOR FORMING A FILTERING FIBER CAKE IN AN APPARATUS FOR MEASURING THE BEATING DEGREE OF PULP FLOWING THROUGH A CONDUIT

[75] Inventor: Henrik Martin Kitsnik, Segmon, Sweden

[73] Assignee: AB Kalle-Regulator, Industrivagen, Saffle, Sweden

[21] Appl. No.: 671,404

[22] Filed: Mar. 29, 1976

[30] Foreign Application Priority Data

Apr. 10, 1975 Sweden ................................ 7504129

[51] Int. Cl.² .......................... D21F 7/06; G01N 15/00
[52] U.S. Cl. ...................................... 162/198; 73/63; 137/92; 162/263
[58] Field of Search ...................... 162/198, 263; 73/63, 73/61 R; 137/91, 92

[56] References Cited

U.S. PATENT DOCUMENTS

| | | | |
|---|---|---|---|
| 3,110,172 | 11/1963 | Irwin | 137/92 |
| 3,186,215 | 6/1965 | Danforth | 162/198 |
| 3,538,749 | 11/1970 | Danforth | 162/198 |
| 3,611,789 | 10/1971 | Lopas | 73/61 R |
| 3,688,563 | 9/1972 | Enarsson et al. | 162/263 |

Primary Examiner—Robert L. Lindsay, Jr.
Assistant Examiner—George C. Yeung
Attorney, Agent, or Firm—Louis Weinstein

[57] ABSTRACT

Apparatus in which a sample of pulp flowing through a conduit is periodically introduced into a cylinder. The pulp is deposited upon the strainer element of a piston assembly so as to form a fiber cake which, after formation, is utilized to test the flow of water therethrough over a predetermined time interval in order to measure the degree of beating of the pulp flowing through the conduit. In order to form a fiber cake upon the piston strainer element in which the layers are of substantially uniform density, water at a pressure higher than that utilized during the test period is introduced into the test cylinder and in a direction substantially tangential to the interior surface of the cylinder in order to set up a rotating flow of fluid facilitating formation of fiber cake layers of uniform density.

6 Claims, 4 Drawing Figures ptdf
METHOD AND DEVICE FOR FORMING A FILTERING FIBER CAKE IN AN APPARATUS FOR MEASURING THE BEATING DEGREE OF PULP FLOWING THROUGH A CONDUIT This invention relates to a method and a device for forming a filtering fiber cake from a withdrawn sample of pulp, the permeability of said fiber cake for water serving as the basis of measuring the degree of beating, especially in an apparatus for measuring the degree of beating of pulp flowing through a conduit.

BACKGROUND OF THE INVENTION

An apparatus for measuring the degree of beating of a fibrous suspension is described in our Swedish Pat. No. 351,927 which corresponds to U.S. Pat. No. 3,688,563. This apparatus may be connected to a conduit for flowing pulp to render possible a periodical withdrawal of samples of pulp and an accurate determination of their beating degree. If desired, the result of measuring may be obtained in ° SR.

The apparatus comprises a vertical sampling cyclinder closed at the bottom end and open at the upper end, and having its upper end connected to a corresponding opening in the lower wall of a substantially horizontal portion of said conduit. A cover plate is mounted above the cylinder so that, when in use, it is disposed within the conduit, the cover plate being movable to and from a position in which the open upper end of the cylinder is kept closed. A piston movable in the cylinder is composed of a strainer disc or plate and a solid disc normally covering the lower side of the strainer disc but movable therefrom to form a space below the strainer disc when the latter reaches its lowest position. A tapping pipe provided with a valve extends from said space to a measuring vessel. A valve controlled fluid pressure conduit is connected to the upper end of the cylinder, whereby when, in use, the apparatus is connected to the conduit, a sample of pulp filling the cylinder may be dewatered under pressure when the upper end of the cylinder has been closed by the cover plate. The amount of water removed from the sample of pulp, which is collected in the measuring vessel, may be used as a measure of the degree of beating of the pulp.

Irrespective of the choice of pressure fluid (gas or liquid), it is of essential importance for a reliable result that the dewatering of the sample of pulp through the strainer disc occurs at a constant pressure. If a liquid is chosen only water under pressure has been found to be useful in practice and in such case it has proved to be of less importance if some of the pressurized water supplied from above in the sampling cylinder mixes with the upper layer of the pulp sample. The explanation thereof may be that a filtering fiber cake is rapidly formed on the strainer disc at the very beginning of the straining operation, and the permeability of the fiber cake for water is then practically independent of the dilution of the filtered suspension. Thus, in this case, the ability of the pulp sample to permit the passage of water is measured.

In laboratory experiments using a transparent cylinder it has now become evident that temporary interferences appear in withdrawal of a sample of pulp from a pulp flowing through a conduit, said interferences result in an uneven distribution of the fiber cake and on certain occasions even direct passage may occur, which, in turn results in incorrect results. The measuring result is also affected if the strainer disc does not completely tighten against the cylinder wall when said disc is in its lowest position.

BRIEF DESCRIPTION OF THE INVENTION

This invention provides a method and a device in an apparatus for measuring the beating degree of pulp of the type described above, by which the mentioned disadvantages are overcome. According to the invention the sample of pulp is treated by a rotating flow of fluid having a pressure greater than the pressure in the conduit during a stirring and/or a dilution period in connection with the withdrawal of the sample and when the sample is withdrawn from the pulp flowing through the conduit the pressure of the flow of fluid is lowered to a predetermined value, which is adapted to the deposit process of the sample of pulp.

This technique assures that the fiber cake is deposited onto the strainer disc in an evenly distributed layer, so that a better and more uniform reproducability in the function of the apparatus is achieved. In addition to yielding a simpler construction which can be manufactured cheaper than what has been the case before, one also obtain a better guidance of the piston in the cylinder. The cleaning of the injection nozzles has also been essentially simplified and effectivized.

BRIEF DESCRIPTION OF THE FIGURES

The invention will now be described by way of example only with particular reference to the accompanying drawings wherein.

Figure 1:
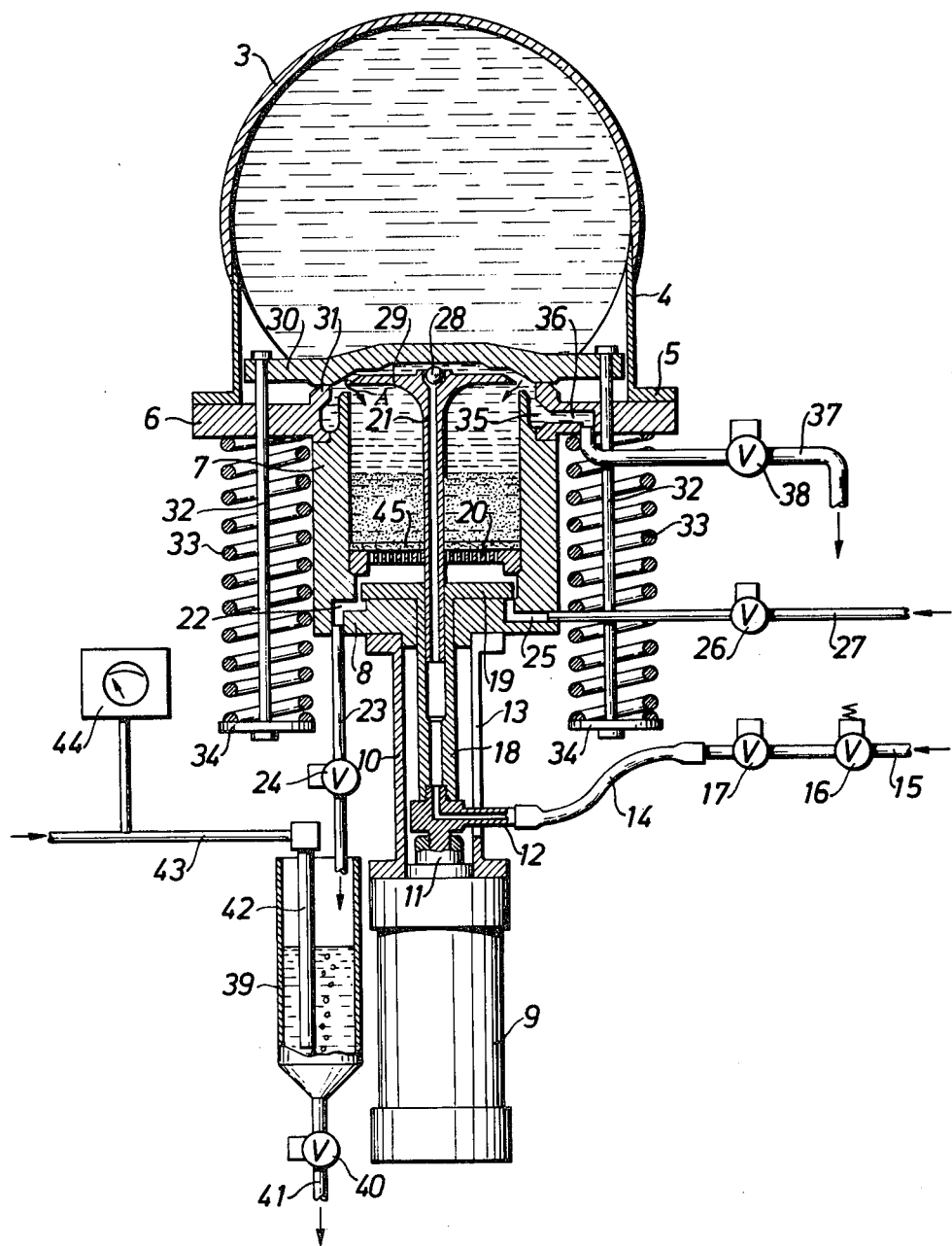
FIGS. 1 and 2 show diagrammatically in vertical section and in two different working positions, an apparatus of the prior art.
Figure 2:
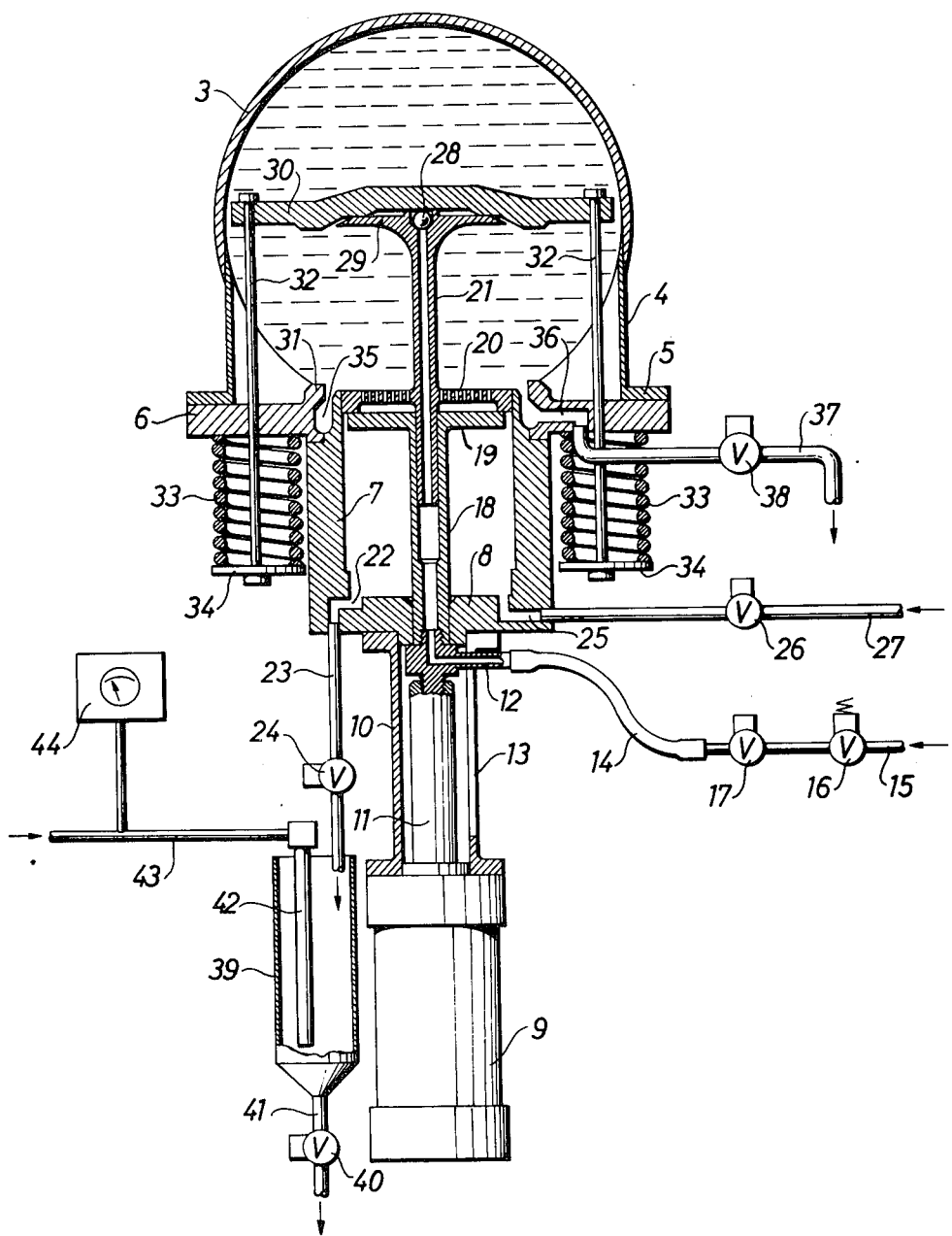

The known apparatus, illustrated in the FIGS. 1 and 2, is mounted beneath a conduit 3 for fibrous suspensions. The conduit 3 has a branch consisting of a short pipe socket 4 welded to its lower side. The free end of the pipe socket 4 has a radial flange 5 to which a ring 6 with a smaller inner diameter than the pipe 4 is secured in any suitable manner (not shown). The ring 6 carries a depending cylinder 7 (hereinafter referred to as the sampling cylinder) releasably mounted thereon. The sampling cylinder 7 has a bottom end wall 8 but is open at its upper end to communicate with the interior of the conduit 3.

A fluid pressure operated double-acting cylinder 9 is carried coaxially in alignment with the sampling cylinder 7 by means of a tubular connection member 10 suspended from the bottom wall 8 of the cylinder 7. The tube 10 encloses with clearance a piston rod 11 extending upwardly from a piston within the driving cylinder 9. The upper end of the piston rod 11 is secured to a right-angled pipe 12, one end of which projects radially through a longitudinal slit 13 in the tube 10. By means of a flexible hose 14 the pipe 12 is connected to a pressure water conduit 15 containing a reduction valve 16 and a shut-off valve 17. The other end of the pipe 12 is threaded externally and screwed into one end of a tubular piston rod extension 18 which sealingly fits in a central opening in the bottom wall 8 of the sampling cylinder 7. Within the sampling cylinder 7 the end of the tube 18 carries a flange or plate 19, the diameter of which is slightly smaller than the smallest inner diameter of the sampling cylinder 7.

A piston which fits inside the sampling cylinder 7 is formed as a strainer plate or disc 20 and has a tubular piston rod 21, the lower end of which is slidably fitted in the upper part of the tubular extension 18. In FIG. 1, the strainer disc 20 is in its lower end position in which it rests on an annular shoulder in the cylinder 7 at such a distance from the bottom wall 8 that a space is formed between the underside of the strainer disc and the upper side of the plate 19, when the latter is in contact with the cylinder bottom wall 8. A channel 22 through the bottom wall 8 connects said space with a downwardly directed outlet pipe 23 containing a shut-off valve 24. Another channel 25 extending through the lower end of the sampling cylinder 7 is connected to a thrust water pipe 27 provided with a shut-off valve 26.

The tubular piston rod 21 extends upwardly through the sampling cylinder 7, and has at its upper end a ball or check valve 28 which opens outwardly. In case a liquid is used as the pressure fluid the check valve 28 may be omitted. Further, the upper end of the rod 21 is widened radially to form a disc-like member 29. In its lower end position shown in FIG. 1, said member 29 is located slightly above the open upper end of the cylinder 7 so that an annular space is formed.

A horizontal cover plate 30 is movable with clearance within the pipe socket 4. In FIG. 1, the cover plate 30 is supported by an annular bead 31 provided around the inner periphery of the ring 6, whereby said cover forms a sealing cover for the sampling cylinder 7. Two vertical guide rods 32 are secured to diametrically opposed points of the cover 30 and extend through corresponding bores in the ring 6. The rods 32 are urged in a downward direction by helical springs 33 which encircle rods 32 and are disposed between the underside of the ring 6 and washers 34 mounted on the ends of the rods 32. By this arrangement, the cover 30 is normally held in sealing engagement with the annular bead 31, and in this position the upper side of the member 29 is positioned slightly spaced below the underside of the cover 30. The arrangement is such that a central space is left around the check valve 28 even if the member 29 is moved upwards until its rim portion engages the underside of the cover 30, as shown in FIG. 2.

An annular space 35 is formed between the inner circumference of the ring 6 and an opposite portion of the outside cylinder 7, and a channel 36 extending radially outward from the space 35 through the ring 6 is connected to discharge conduit 37 containing a shut-off valve 38.

The outlet pipe 23 from the lower end of the sampling cylinder 7 heads into a cylindrical measuring vessel 39 open at the top. A bottom outlet 41 of the vessel 39 is provided with a shut-off valve 40. The measuring vessel 39 may be graduated to indicate the amount of liquid collected, but preferably the liquid level is measured in another way known per se. Thus, a vertically aligned tube 42 extending into the vessel 39, is connected to a conduit 43 through which a weak flow of air is supplied. The pressure variations in the conduit 43 caused by varying liquid levels in the vessel 39 are indicated by a pressure meter 44 connected to the conduit and, if desired, graduated to indicate the degree of beating directly in ° SR.

The beating degree meter described above operates as follows. Initially, the various movable parts are in the positions shown in FIG. 1 except that the sampling cylinder 7 is filled with rinsing water. The valve 24 and the valve 40 of the measuring vessel are closed in this initial position, but the valves 17, 26 and 38 in the conduits 15, 27 and 37, respectively, are open. The pressure reduction valve 16 in the compressed water conduit 15 has been adjusted at a comparatively low constant overpressure which, in respect to the average concentration of pulp, may vary between 0.4 and 1.0 atm. gauge, for instance.

In preparation for a testing operation, pressure fluid is supplied to the cylinder 9 so that its piston rod 11 moves upwards and at the same time the valves 26 and 38 are closed, but the valves 24 and 40 are opened, so that the measuring vessel 39 is emptied. The cover plate 19 engages the underside of the strainer disc 20 in the sampling cylinder 7, and the two plates 19 and 20 form a solid piston which move upwardly as a unit. During this continued movement the member 29 engages the cover plate 30 and lifts it against the action of the springs 33 into the upper position shown in FIG. 2, where the piston 19, 20 is positioned at the upper end of the sampling cylinder 7. In this position the flow of pulp through the conduit 3 passes freely between the upper side of said piston and the underside of the cover 30. When a sample of pulp is to be withdrawn for determination of the beating degree, the supply of pressure liquid to the cylinder 9 is altered so that the piston rod 11, 18 with the cover plate 19 moves downward and the other movable parts also move downwards because of the force exerted by the springs 33 on the cover 30. When the cover 30 has resumed the closing position shown in FIG. 1, a volume of pulp to be tested has been enclosed in the cylinder 7 between the piston 19, 20 and the cover 30. Owing to the overpressure prevailing in the space between the member 29 and the cover 30 the member 29 and the strainer disc 20 are moved still further downwards, and thus the compressed water supplied by the conduit 15 flows into the cylinder 7 (see arrows A) and acts upon the upper surface of the pulp column located therein. The strainer disc 20 is halted in its lower end position described above, while the piston rod 11, 18 moves the cover plate 19 into contact with the bottom of the cylinder 7. When a space has thus been established below the strainer disc 20, water begins to escape from the pulp and the water flows through the pipe 23 down into the measuring vessel 39 and a fiber cake 45 beings to form on the strainer disc 20. At a certain pre-determined time the bottom valve 40 of the measuring vessel 39 is closed so that the water is collected in the measuring vessel 39 and at a pre-determined point of time thereafter the draining valve 24 is closed. Then the vessel 39 contains the amount of water that has been drained off under the influence of a pre-determined drop in pressure during the period of time in question. As mentioned, the cooperating factors, the pressure of the fluid, time of draining etc., may be determined such that the result is obtained in ° SR on the pressure meter 44.

When the draining valve 24 has been closed, the valve 26 in the thrust water conduit 27 and the valve 38 in the outlet conduit are opened to remove the pulp tested. Although not shown in the drawing, a pressure air conduit controlled by a valve may open into the water conduit 27 so that the washing or rinsing water is mixed with air bubbles before reaching the underside of the strainer disc 20. Such a mixture of water and air has proved to effect a particularly efficient cleansing of the strainer. The washing is continued for a pre-determined period of time until the next testing operation, when the described procedure is repeated.

If desired, the various valves in the apparatus except for the pressure reduction valve 16 may be controlled by a programming mechanism which initiates the desired operations at the desired moments.

As mentioned above, the sampling cylinder 7 may be releasably mounted in the ring 6, although the arrangement therefore is not shown. Such a mounting has the advantage that the entire apparatus can be removed for maintenance or repair without disturbing the normal operation of the plant, as the opening in the ring 6 is kept closed by the cover 30.

Figure 3:
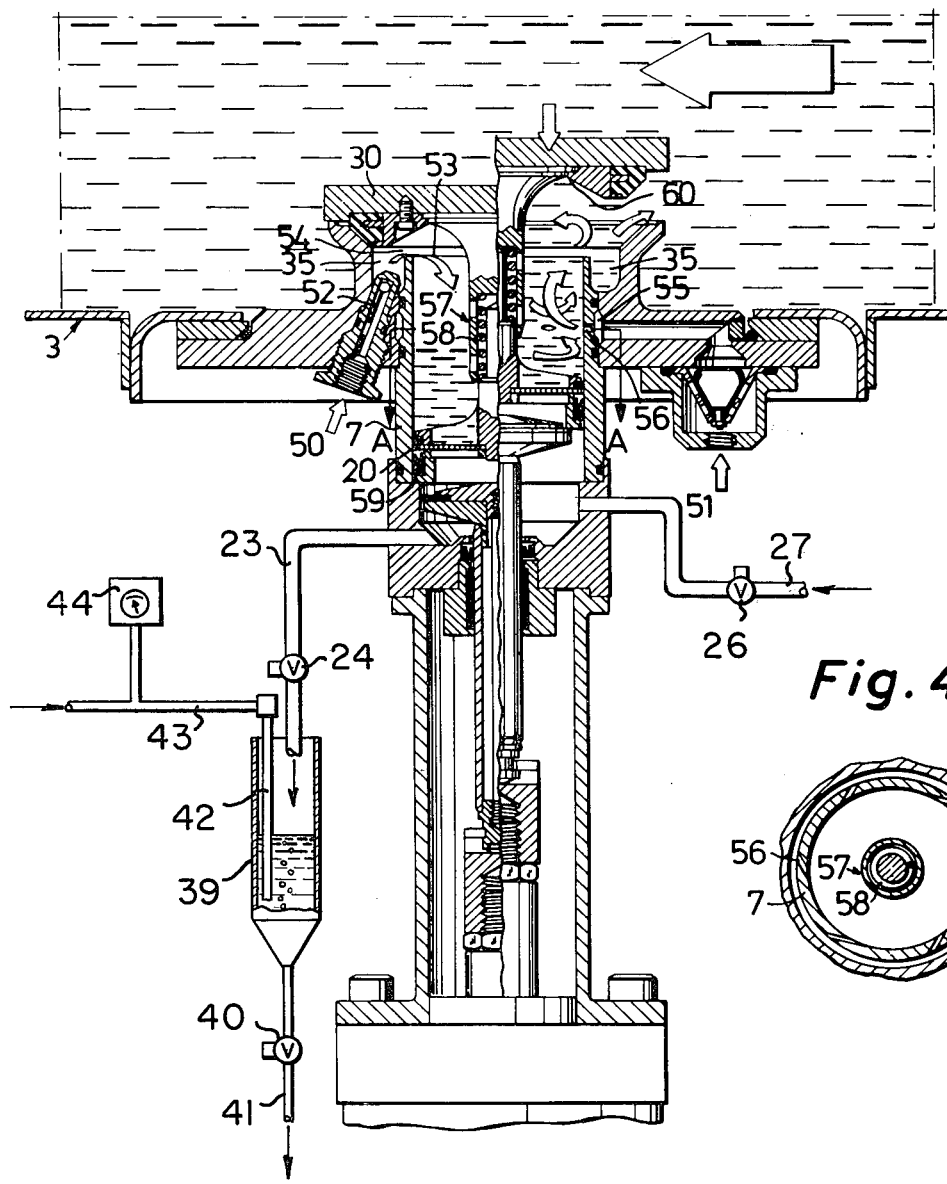
FIG. 3 shows also diagrammatically in vertical section and in two different working positions, the device according to the present invention.
Figure 4:
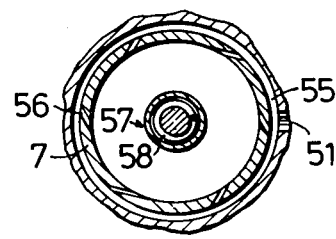
FIG. 4 is a section on the plan A—A of FIG. 3.

As principally can be seen from FIGS. 3 and 4, the present invention relates to a method to form or obtain a filtering fiber cake of uniform thickness. In performing the method a sample of pulp, which is withdrawn from a fibrous suspension flowing through a conduit, is treated by a rotating flow of fluid. During a stirring and/or a dilution period in connection with the withdrawal of the sample, said rotating flow of fluid has a pressure exceeding the pressure in the conduit. When the sample is withdrawn from the pulp flowing in the conduit, the pressure of the flow of fluid is lowered to a predetermined value adapted to the deposit process of the sample of pulp.

A suitable device for performing the method is illustrated in FIGS. 3 and 4. Said device corresponds basically with the known apparatus, illustrated in the FIGS. 1 and 2, and therefore only that part is included which directly concerns the present invention. As can be seen from the drawings the most essential difference is the supply of the flow of fluid. In the embodiment illustrated said flow is supplied either through a conduit 50 or through a conduit 51. The supply of a flow of fluid, for instance water under pressure (thrust water) through the conduit 50, occurs when the concentration of the pulp flowing through the conduit 3 maintains a value which is below approx. 4%. The conduit 50 terminates in a nozzle 52, which opens tangentially into an annular space 35 surrounding the upper portion of the cylinder 7. Said space 35 communicates, in turn, with the interior of the cylinder 7 by an opening 54, extending around an upper edge 53 of the cylinder 7. The opening of the nozzle 52 has a diameter of approx. 3–4 mm.

When the pulp flowing in the conduit 3 has a concentration exceeding approx. 4%, supply of thrust water takes place through the conduit 51, which communicates with an annular channel 55 located around the cylinder 7 at its upper part and just below the annular space 35. The channel 55 communicates with the interior of the cylinder 7 by a number of mouths and nozzles 56. In this embodiment six essentially tangential nozzles 56 extend through the cylinder wall. In this embodiment the diameter of the nozzles 56 is approx. 2–3 mm. In testing operations where the concentration of the pulp exceeds approx. 4% the cover plate 30 is lowered at a rate which is slower than the lowering rate in the known apparatus illustrated in the FIGS. 1 and 2, so that a desired dilution and stirring of the sample can take place in the cylinder 7 before the cover plate 30 has been completely closed. The cover plate 30 is connected by piston rod 57 to the strainer disc 20. The piston rod 57 consists of two parts which are telescopically displaceable into each other, said parts being actuated in a direction away from each other by a screw spring 58 operating between said parts after compressing of the two parts into each other a certain distance. Hereby strainer disc 20 is spring activated toward its lower end position in the cylinder 7 to provide an effective seal of the periphery of the strainer disc 20 against an annular stop flange 59 projecting from the cylinder wall and close to the bottom of the cylinder when said disc 20 is in its lower most position in the cylinder 7.

The beating degree meter described above operates mainly in the same way as the known apparatus illustrated in the FIGS. 1 and 2. The conduits 50 and 51 are also provided with valves for controlling the pressure of the thrust water. At the testing operation a stabilization of the fiber cake occurs, in conformity with what has already been described above about the known apparatus, after the withdrawal of the sample and before the real measurement is started by allowing water to pass through the fiber cake during a certain period of time after the fiber cake has formed upon the strainer disc 20.

During removal of the pulp tested the conduits 50 and 51 are used in addition to the thrust water conduit 27 connected to the bottom of the cylinder, through which conduits water is supplied at a high pressure so that an effective removal of pulp tested is attained. Owing to a tray formation 60 of the under side of the cover 30, said formation 60 extending around the periphery of the cover close to its outer edge the removal of pulp tested is further facilitated.

Although there has been described a preferred embodiment of this novel invention, many variations and modifications will now be apparent to those skilled in the art. Therefore, this invention is to be limited, not by the specific disclosure herein, but only by the appending claims.

What I claim is:

1. A method utilizing a porous strainer disc for forming a fiber cake from a sample of a fibrous suspension, comprising the steps of:

withdrawing a sample of a fibrous suspension from a conduit through which said suspension flows and introducing said suspension into a sampling vessel containing the disc so that the suspension enters on one side of the disc;

introducing a fluid into said vessel and on the same side of said disc at a first pressure greater than the pressure of said suspension flowing through said conduit as said suspension is being introduced into said vessel, said fluid being introduced into said vessel in a direction which is substantially tangential to the wall of the vessel to cause rotation of said suspension about the longitudinal axis of said vessel to form a fiber cake of even density upon said disc;

draining the fluids from the vessel;

introducing said fluid into said vessel at a second predetermined pressure, which is lower than said first pressure, upon the fiber cake formed upon said disc in said vessel;

measuring the rate of flow of fluid per unit time through the fiber cake to determine the degree of beating of the pulp flowing through the conduit.

2. Apparatus for forming a pulp cake from a sample of a fibrous suspension flowing through a conduit, said apparatus comprising:

a sampling cylinder connected to said conduit and containing a straining disc on which said pulp cake is to be formed, said sampling cylinder being closed at a first end and open at a second end, said second end is connected to a corresponding opening in said conduit;

means for introducing a sample of said suspension flowing through said conduit into said sampling cylinder;

means for causing said suspension to flow through said straining disc so as to form a pulp cake thereon;

at least one valve controlled conduit for introducing a fluid under pressure into said cylinder in a direction which is substantially tangential to wall of the sampling cylinder to cause rotation of said suspension about the longitudinal axis of said cylinder as said suspension is introduced into said cylinder whereby a pulp cake of substantially uniform density is caused to form on said straining disc.

3. Apparatus according to claim 2 including an annular space (35) formed in said apparatus and located outside the upper part of said cylinder (7), said annular space (35) communicating with the interior of said cylinder (7) via an opening (54) extending around an upper edge (53) of said cylinder (7) and formed in said apparatus, said apparatus further including a fluid pressure conduit (50) terminating in a nozzle (52) extending into said annular space (35) and having an outlet opening arranged to emit fluid therefrom in a direction substantially tangential to the cylinder wall.

4. Apparatus according to claim 3, wherein said at least one valve controlled conduit comprises a fluid pressure conduit (51) communicating with an annular channel (55) formed in said apparatus and located around the upper portion of the sampling cylinder (7) and just below said annular space (35), said channel (55) communicating with the interior of the cylinder (7) by a number of essentially tangentially aligned mouths or nozzles (56) extending through the cylinder wall.

5. Apparatus according to claim 2, wherein said sample introducing means comprises a cover plate and piston means for moving said cover plate between a first position sealing the opening between said conduit and the sampling cylinder and a second position displaced from the opening;

spring means positioned between said cover plate and said strainer disc whereby said strainer disc, upon which a fiber cake is to be formed, is spring actuated towards its lower end position in said cylinder (7) in sealing engagement with an annular stop flange (59) projection from an interior cylinder wall close to the bottom of said cylinder (7).

6. Apparatus according to claim 2 including means for introducing fluid under pressure into said cylinder via said at least one valve controlled conduit at a first pressure greater than the pressure of said suspension flowing through said conduit as said suspension is being introduced into said cylinder and at a second, predetermined pressure which is lower than said first pressure a predetermined time after said suspension has been introduced into said cylinder.

* * * * *